(12) United States Patent
Kraus et al.

(10) Patent No.: US 7,227,633 B2
(45) Date of Patent: Jun. 5, 2007

(54) OPTICAL SUBSTRATE FOR ENHANCED DETECTABILITY OF FLUORESCENCE

(75) Inventors: Jörg Kraus, Lindau (DE); Johannes Edlinger, Feldkirch (AT); Max Wiki, Zurich (CH); Heidi Thome-Forster, Azmoos (CH); Claus Heine-Kempkens, Chur (CH); Bernd Maisenhoelder, Zurich (CH); Martin Kaspar, Mels (CH)

(73) Assignee: OC Oerlikon Balzers AG, Balzers (LI)

( * ) Notice: Subject to any disclaimer, the term of this patent is extended or adjusted under 35 U.S.C. 154(b) by 0 days.

(21) Appl. No.: 10/858,792

(22) Filed: Jun. 2, 2004

(65) Prior Publication Data

US 2004/0247485 A1 Dec. 9, 2004

Related U.S. Application Data

(60) Provisional application No. 60/539,872, filed on Jan. 28, 2004, provisional application No. 60/475,395, filed on Jun. 3, 2003.

(51) Int. Cl.
- *G01N 21/64* (2006.01)
- *G01T 1/10* (2006.01)
- *G02B 5/28* (2006.01)

(52) U.S. Cl. .............. 356/244; 356/630; 250/458.1; 359/884

(58) Field of Classification Search .............. 356/244, 356/246, 317–318; 250/458.1, 214.1, 453.11, 250/353; 359/321, 260, 558, 360, 584; 436/172
See application file for complete search history.

(56) References Cited

U.S. PATENT DOCUMENTS 3,858,046 A * 12/1974 Cubalchini .................. 250/353
4,147,409 A * 4/1979 Apfel ......................... 359/584
4,284,897 A 8/1981 Sawamura
4,408,825 A * 10/1983 Stelmack .................... 359/360
4,441,789 A * 4/1984 Pohlack ...................... 359/588
4,877,965 A 10/1989 Dandliker
5,091,652 A 2/1992 Mathies
5,091,653 A 2/1992 Creager
5,095,213 A 3/1992 Strongin
5,257,140 A * 10/1993 Rogers ....................... 359/884
5,296,700 A 3/1994 Kumagai
5,381,224 A 1/1995 Dixon
5,504,336 A 4/1996 Noguchi
5,552,272 A 9/1996 Bogart
5,646,411 A 7/1997 Kain
5,672,880 A 9/1997 Kain
5,847,400 A 12/1998 Kain
6,008,892 A 12/1999 Kain
6,177,990 B1 1/2001 Kain et al.
6,335,142 B1 * 1/2002 Quesnel et al. ........... 430/275.1
6,867,900 B2 * 3/2005 Weisbuch et al. ........... 359/321
2004/0092028 A1 * 5/2004 Chaton et al. .............. 436/172

FOREIGN PATENT DOCUMENTS

| WO | 02/48691 A | 6/2002 |
| WO | WO 03/025553 A2 * | 3/2003 |
| WO | WO 02/48691 A1 * | 6/2003 |

* cited by examiner

*Primary Examiner*—Sang M. Nguyen
(74) *Attorney, Agent, or Firm*—Pearne & Gordon LLP (57) ABSTRACT

A sample substrate adapted for use with fluorescence excitation light with a first wavelength. A reflector is disposed on a base. The reflector includes a reflecting multilayer interference coating with at least two layers. Not all of the layers L fulfill a quarterwave condition: $dL \cdot nL = (2N+1) \cdot 1/4$ wherein dL is a physical thickness of layer L, nL is an index of refraction of layer L at the first wavelength, N is an integer equal to or greater than zero and 1 is the first wavelength. Thicknesses of the layers ensure that any fluorescent sample material disposed on top of said multilayer interference coating would be located near an antinode of a standing wave formed by the excitation light with the first wavelength incident on said substrate.

21 Claims, 2 Drawing Sheets

OPTICAL SUBSTRATE FOR ENHANCED DETECTABILITY OF FLUORESCENCE

BACKGROUND OF THE INVENTION

The present invention relates to sample substrates, such as plates, slides and cells, for use in examining, indicating, analyzing or identifying fluorescent, phosphorescent or luminescent sample materials, e.g. tagged molecular biological specimens, and in particular relates to such sample holders whose optical structures are adapted for enhancing fluorescence detection and imaging. The format of the sample substrates of the present invention can be adapted to formats typically used in this field, such as for example the standard format of microtiter plates.

Fluorescence microscopy is often used in the fields of molecular biology, biochemistry and other life sciences for analyzing biological molecules, including nucleic acids (DNA, RNA) and proteins (enzymes, antigens, etc.) that have been tagged or labeled with fluorescent probes. One such use is DNA diagnostics, such as for gene detection, in which a DNA sample is deposited on and bound to a glass substrate. The bound DNA on the substrate can then be imaged by fluorescence. The fluorescence of a sample was originally assessed by visual inspection through a conventional microscope, but this manual method has proved time-consuming and costly. Many different high-speed automated fluorescence imaging systems are now available.

An important figure of merit for fluorescence detection and measurement instruments is sensitivity, which is primarily determined by the signal-to-noise ratio (SNR) of the optical imaging system of the instrument. A well-designed imaging system has a signal-to-noise ratio that is limited by its light collection ability and not by internal noise sources. The theoretical SNR of such a system is expressed in terms of the number of photoelectrons at the cathode when using a photomultiplier tube (PMT), which in turn essentially depends upon the number of photons that reach the detector from the area of interest on the sample substrate, the quantum efficiency of the detector, and the number of dark electrons generated by the detector.

One obvious approach to increasing SNR, and thereby improving sensitivity, is to reduce background noise. Sources of background noise include specular or diffuse reflection of the fluorescence-stimulating laser light from the sample, autofluorescence of the substrate holding the sample, autofluorescence from the optics in the light path of the optical imaging system, stray light, and dark current of the detector. Stray light reaching the detector can be significantly reduced by proper size and placement of apertures in the imaging system. Both stray light and much of the reflected laser light can be rejected, while passing the fluorescent light, by using dichroic and other spectral filters and beamsplitters in the system. Autofluorescence of the optical elements can be reduced by avoiding use of lens cements in the light path, using glass instead of polymeric lenses, or using curved mirrors instead of lenses wherever possible.

Autofluorescence of the substrate can be reduced by using low fluorescence materials, such as an ultrathin or opaque glass substrate. For example, in U.S. Pat. No. 5,095,213 Strongin discloses a plastic slide that is rendered opaque and substantially nonfluorescent with a quantity of black carbon powder in the plastic. Another way of handling autofluorescence is to use a pulsed or modulated excitation and to take advantage of the differences in emission decay rates between background fluorescence and specimen fluorescence, as disclosed in U.S. Pat. No. 4,877,965 to Dandliker et al. and U.S. Pat. No. 5,091,653 to Creager et al.

In U.S. Pat. No. 5,552,272, Bogart discloses an assay system and method for detecting the presence or amount of an analyte of interest. It includes a test substrate with an optically active surface that enhances the color contrast, i.e. differences in the observed wavelength (or combination of wavelengths) of light from the surface, between the presence and absence of the analyte in a sample applied onto the test substrate. In particular, the substrate may comprise a reflective solid optical base, such as a silicon wafer or metallic (e.g., aluminum) base, with an optical thin film coating thereon. The coating may comprise several layers, including for example an attachment layer on the upper surface of the base, and a receptive layer on the upper surface of the attachment layer containing a specific binding partner for the analyte of interest. The total coating thickness is selected to cause incident light to undergo thin film interference upon reflection, such that a specific color is produced. Specifically, the coating material(s) should have an overall thickness of a quarterwave of the unwanted color to be attenuated so that destructive interference of that color will occur. The substrate therefore has a particular background color, which can then be used as a comparative reference against a different observed color when an analyte of interest is present. Both qualitative visual inspection and quantitative instrumented measurement are suggested. Polarization contrast by means of an ellipsometer is also suggested.

One example of the use to which the Bogart invention has been put by Biostar, Inc. of Boulder, Colo., the assignee of the aforementioned patent, is an optical immunoassay (OIA) diagnostic screening test for the rapid detection (in under 30 minutes) of the presence of specific antigens of infectious pathogens in a sample taken from a patient. Commercial products include test kits for group A and group B streptococci and for *chlamydia trachomatis*. These particular assays are given as examples in the Bogart patent, are described in package inserts for the corresponding Biostar products and are also described in a number of published articles in medical journals. Briefly, they all rely on direct visual detection of a change in the color of light reflection off of the test substrate due to a physical change in the optical thickness of a molecular thin film coating on the substrate surface which results from binding reactions between an immobilized antibody on the test surface and a specific antigen that may be present in a drop of sample liquid applied to the test surface. The original bare test surface has a thin film thickness that results in a predominant visual background gold color when white light is reflected off of the surface. The antigen-antibody binding reaction that occurs when the specific antigen of interest is present in the applied sample results in an increase in the thin film thickness that causes a corresponding change in the color of the test surface from gold to purple. If on the other hand, the antigen is not present in the sample, no binding takes place, the original thin film thickness remains unchanged and the test surface retains its original gold color, indicating a negative result. This diagnostic assay tool is very sensitive and easily interpreted.

Bogart further discloses, in another embodiment of his invention (FIG. 17 of the aforementioned patent), the use of these substrates for enhanced fluorescence detection. After the analyte of interest has been bound to the surface by reaction with the specific binding partner in the receptive layer of the substrate coating, fluorescent label molecules may be attached to the analyte. In particular, the fluorescent molecules may be attached to any suitably selective and specific receptive material or reagent, such as a secondary antibody, and applied to the surface. The fluorescent labels are thus bound to the analyte of interest on the surface, if present, and immobilized to the surface through the analyte bridge. Directing light of an excitation wavelength onto the surface stimulates fluorescence of any of the label bound to the surface, thereby revealing the presence of the analyte of interest. Because the maximum fluorescence wavelength may not be shifted far enough from the excitation wavelength to be distinguished, the reflective substrate may have an antireflection layer whose thickness is selected to suppress reflection of the excitation wavelength, thereby reducing the background noise reaching the detector. Bogart states that the fluorescent signal generation is not dependent on the film thickness. Though the fluorescence signal S might be increased by increasing the output power of the laser, reflected laser noise will also increase, with possibly little improvement in the resulting SNR.

In U.S. Pat. No. 6,008,892 Kain et al disclose a sample substrate which is reflective for the excitation wavelength. This substrate has a transparent coating layer thereon with controlled thickness that has been selected to ensure that a molecular sample placed on top of the coating layer is located at an antinode for the excitation light. In particular, the substrate includes a rigid base with a specularly reflective upper surface. The transparent coating on the upper surface of the base has a thickness selected such that for a particular excitation wavelength of light at normal incidence, the optical path from the top of the coating to the base reflecting surface is substantially an odd multiple (1, 3, 5, etc.) of one-quarter wavelength of the excitation light. The optical path length of the material is defined by the wavelength of light, the index of refraction of the material, and the angle of propagation through the material. In the reflective sample substrate the reflecting surface of the base is at a well defined depth slightly below the physical surface of the base by an amount equal to the sum of the skin (or penetration) depth of the reflective surface material and the optical depth of any surface oxidation on the base. By placing the sample on the coating layer at or near the antinode of the excitation light, maximum fluorescence excitation occurs. A reflective substrate also enhances fluorescence collection by nearly doubling the solid collection angle of a fluorescence imaging microscope system. Thus, the total fluorescence signal is increased, leading to a much improved signal-to-noise ratio. Also, because the coating layer is very thin, there is reduced fluorescence background noise from this material.

As Kain et al describe the base can be made completely of metal or may be composed of a rigid bottom layer with a top metal coating. The metal can be aluminum, silver, gold or rhodium. The transparent coating may be a single layer of dielectric material, such as silica, alumina or a fluoride material (such as $MgF_2$). Alternatively, the transparent coating could be a multilayer coating with the top layer being a chemically reactive material for binding a specified biological sample constituent thereto.

Kains concept of applying a transparent quarterwave layer on a reflecting surface is limited to reflectors with rigid surfaces. Here light is not penetrating beneath the physical surface of the reflector or the penetration is limited to at most some nanometers beneath the surface (skin depth). Practically this represents a limitation to metallic surfaces such as metal substrates or metallic coatings.

As soon as dielectric layers significantly contribute to the reflection, it is difficult to define a penetration depth and the concept of adding a quarterwave layer fails. For example for aluminum mirrors very often additional dielectric layers are used to enhance the reflectivity of the metal which results in so called "pumped metallic mirrors". In this case the dielectric layers are part of the mirror and the last dielectric layer forms the physical surface of the mirror. Light penetrates into such a mirror stack and interference effects together with the metallic reflectivity establish the optical characteristics. Adding an additional quarterwave layer or an odd multiple to such a system very often fails to produce an antinode at the location of fluorescent sample when placed on this layer. In addition in most cases the interference system is disturbed which might result in a drastic decrease of reflectivity.

However as long as the odd multiple quarterwave condition is fulfilled with respect to the metallic surface it is even possible to enhance fluorescence using the reflectivitiy contribution of the quarterwave layers. Chaton et al give one example in WO 02/48691 where this effect can be seen. Chaton et al describe the use of dielectric quarterwave stacks which have a mirror function on a silicon substrate in order to enhance the fluorescence. The reflectivity of silicium at 550 nm is at about 42%. This results in a square electromagnetic field amplitude ($E^2$) on the metallic surface of about 10% of the square of the field amplitude of the free propagating wave $E^2(PW)$. Applying a single quaterwave layer of $SiO_2$ on that rigid metallic surface (following one embodiment of the invention of Kain et al) results in a field amplitude which is 25% higher than $E^2(PW)$ therefore resulting in an enhancement factor of 1.25. Chaton et al use a quarterwave stack with a design wavelength of 550 nm in order to reinforce reflectivity. This means that a system of alternating high and low index dielectric layers is used to increase the reflectivity, where each individual layer has an optical thickness of one quarter of the design wavelength. As an example Chaton et al use a five layer system on silicon with $SiO_2$ (94 nm layer thickness, 3 layers) and $Si_3N_4$ (69 nm layer thickness, 2 layers) as coating materials. This results in a reflectivity of slightly below 60%. Mirrors based on quarterwave stacks are known as Bragg mirrors. Typically such a Bragg mirror is based on a quarterwave stack where the outermost layer is a high index layer. However Chaton et al use as outermost quarterwave layer an $SiO_2$ layer, which is the low index material. It is known that the outermost layer being a low index layer results in lower reflection values. Removing the outermost layer (low index layer) would even result in higher reflectivity. As the Chaton et al describe they use $SiO_2$ as outermost layer in order to create a physical surface which is compatible with the linker chemistry. However there is one additional positive effect the authors did not mention: Our investigations showed that using a low index layer as outermost layer results in a field amplitude for 550 nm on the surface which is fortunately maximum, 220% more than $E^2(PW)$ resulting in an enhancement factor of 2.2. If the authors had used a high index layer as outermost layer the electromagnetic field amplitude would have been minimum.

With a coating design as used by Chaton et al the reflection band is centered at the design wavelength of 550 nm and is 200 nm broad. Within the reflection band the reflectivity is increased to slightly below 60%. Because Chaton et al did not take into account the antinode condition, they conclude that the quarterwave stack is effectively enhancing the fluorescence signal for wavelengths between 450 nm to 650 nm. This wavelength range comprises the wavelengths of the fluorescence materials typically used for fluorescence lables such as CY3 and CY5. Unfortunately only for the design wavelength the antinode condition is well fulfilled. For an excitation wavelength much different from 550 nm this condition is not fulfilled. For 450 nm the enhancement factor is as low as 0.2 and for 650 nm the enhancement factor decreases down to 1.2.

It is therefore still a problem and would be desirable to create a sample which provides optimum enhancement for more than one excitation wavelength well separated from each other. Especially for the excitation wavelengths around 532 nm–548 nm (Cy3) and around 633 nm (Cy5) it is still an open question how to realize such a sample substrate.

Typically there is an inherent difference of signal intensity for Cy3 and Cy5 related for example to differences in affinity of the linker chemistry, resulting in different signal intensities. Therefore the question of how to realize for two or more excitation wavelengths approximately the same degree signal intensities may be important. It is an interesting, but even more general aspect to consider the possibility to adjust the enhancement factors for two or more excitation wavelengths independently.

In addition as discussed, the prior art solutions involve in general interfaces to metallic layers or substrates. Chaton for example restricts the discussion to a silicon substrate. Examples for rigid reflecting surfaces in Kains disclosure always involve metallic surfaces. It is therefore still a problem and would be desirable to create a substrate sample providing enhanced fluorescence signal without use of a metallic interface as do Kain et al as well as Chaton et al.

Provided is a sample substrate adapted for use with fluorescence excitation light with a first wavelength. A reflector is disposed on a base. The reflector includes a reflecting multilayer interference coating with at least two layers. Not all of the layers L fulfill a quarterwave condition: $d_L \cdot n_L = (2N+1) \cdot \lambda/4$ wherein $d_L$ is a physical thickness of layer L, $n_L$ is an index of refraction of layer L at the first wavelength, N is an integer equal to or greater than zero and $\lambda$ is the first wavelength. Thickness of the layers ensure than any fluorescent sample material disposed on top of said mulitlayer interference coating would be located near an antinode of a standing wave formed by the excitation light with the first wavelength incident on said substrate.

BRIEF SUMMARY OF THE INVENTION

It is therefore an object of the present invention to provide an improved sample substrate which provides increased sample excitation and fluorescence emission without the disadvantage to base the reflection of the excitation wavelength completely on the reflectivity of a metal surface. It is another important aspect of the present invention to disclose a sample substrate providing maximum enhancement of the fluorescence signal for two or more different excitation wavelengths. It is yet another aspect of the present invention to disclose a sample substrate providing application adjusted enhancement factors for two or more excitiation wavelengths.

Provided is a sample substrate adapted for use with fluorescence excitation light with a first wavelength. A reflector is disposed on a base. The reflector includes a reflecting multilayer interference coating with at least two layers. Not all of the layers L fulfill a quarterwave condition: $(dL \times nL) = (2N+1) \times \lambda/4$ wherein dL is a physical thickness of layer L, nL is an index of refraction of layer L at the first wavelength, N is an integer equal to or greater than zero and $\lambda$ is the first wavelength. Thicknesses of the layers ensure that any fluorescent sample material disposed on top of said multilayer interference coating would be located near an antinode of a standing wave formed by the excitation light with the first wavelength incident on said substrate.

The object has been met with a reflective sample substrate comprising an interference reflector based on a dielectric multilayer coating. The excitation light is reflected with 100% or close to 100%. The resulting electromagnetic field distribution connected to the excitation wavelength outside the sample substrate in the cover region is therefore a standing wave or close to a standing wave with planes of nodes and planes of antinodes. In the present invention the layers of the interference reflector have an optimized thickness distribution that has been selected to ensure that an areal fluorescent sample placed on top of the top coating layer is located in the plane of an antinode of the excitation light.

In this case no quarterwave-thickness requirement for the dielectric layers have to be fulfilled. This gives an additional degree of freedom for the design and the maximum or the desired electromagnetic field can be realized on the physical surface even for two or multiple excitation wavelengths. To be more specific, skipping the condition of using quarterwave layers or odd multiples of quarterwave dielectric layers leads to an additional degree of freedom in the design which can be used to fulfill antinode conditions for two or more excitation wavelengths without the need for compromise as is the case for prior art solutions. This degree of freedom can be used for samples where metallic reflecting interfaces are involved as well as for pure dielectric reflectors leading to which are until now not we did not find in prior art solutions.

The electrical field distribution within such an interference reflector is very different from the field distribution known from specular reflection of a metal surface. An additional layer added on top of the interference reflector can cause a decrease in reflectance. In addition for such an interference reflector it is not possible to define the location of a reflection surface since most of coating layers contribute to the reflection.

However we found during our studies and experiments that, despite the difficulty to define a reflection surface, it is possible to design an interference reflector in such a way, that there is a maximum field at the physical surface of the reflective sample substrate where the areal fluorescent sample is placed. The design can be found with the help of standard thin film optimization tools, slightly modified to optimize for maximum reflectivity together with maximum field amplitude at the surface of the reflective sample substrate.

In this case no additional transparent layer is required, no quarterwave-thickness requirement for the dielectric layers have to be fulfilled, so the maximum field can be realized even for two or multiple excitation wavelengths. In addition such a system can preferably be realized without the use of metal layers or a metal substrate at all.

As already mention such systems can be found using statistical techniques as used typically for optical thin film design, modified to take into account as a part of the optimization target the antinode condition on the physical surface. However we investigated the electromagnetic field distribution within the substrate samples we had optimized with the help of such an optimization procedure. We investigated the sample substrates providing enhanced maximum electromagnetic field intensity at the physical surface of the sample for various designs including prior art solutions as disclosed by Kain et al as well as Chaton et al. We found that the electromagnetic field distribution provides a minimum which is located one quarterwave below the physical surface. This was independent how deep actually the electromagnetic field propagates into the samples. As a conclusion we think that the generalization to Kains quarterwave rule is that the electromagnetic field needs to provide a minimum which is located approximately one quarterwave beneath the physical surface. This reflects one aspect of the present invention: As long as the substrate sample provides a minimum in the electromagnetic field distribution located approximately one quarterwave beneath the physical surface the eletromagnetic field on the physical surface will be enhanced.

DETAILED DESCRIPTION OF THE INVENTION

The sample substrate of the present invention can be used in any of a wide number of possible fluorescence microscope systems, including, for example, those described in U.S. Pat. No. 4,284,897 to Sawamura et al., U.S. Pat. No. 5,091,652 to Mathies et al., U.S. Pat. No. 5,296,700 to Kumagai, U.S. Pat. No. 5,381,224 to Dixon et al., and U.S. Pat. No. 5,504,336 to Noguchi, as well as U.S. patent application Ser. Nos. 08/595,355, 08/616,174 and 08/791,684.

Figure 1:
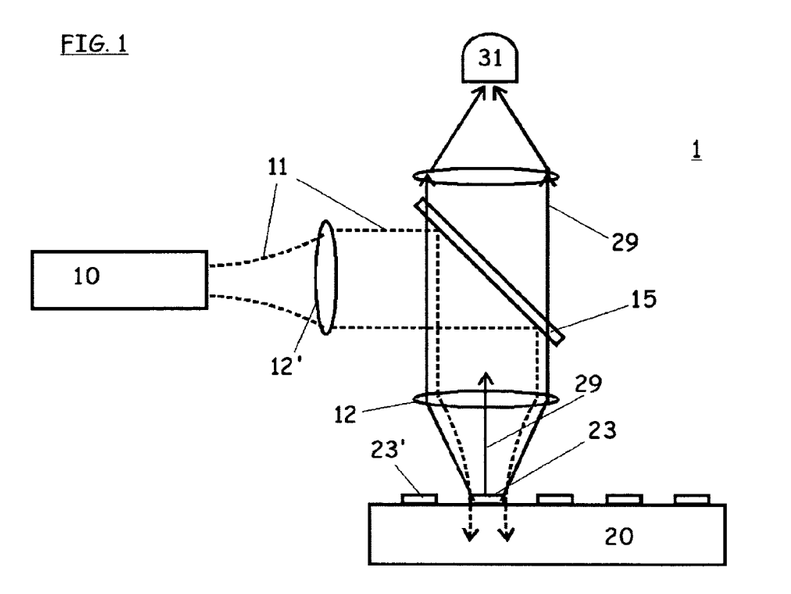
FIG. 1 is a schematic drawing of a fluorescence imaging system as typically used.

A preferred fluorescence imaging system 1 for use with the present invention is illustrated in FIG. 1: A light source 10, for example a laser, produces an stimulating beam 11. The stimulating beam 11 is preferably a collimated beam of monochromatic coherent light. However, a noncoherent source, such as a light emitting diode (LED) could be used and a noncollimated source could be coupled to collimating optics to create a collimated beam. If the stimulating beam 11 is not monochromatic, it may be directed through a filter to reduce any unwanted wavelengths.

The stimulating beam 11 is then directed through lens systems 12, 12' and a beam splitter 15 onto the surface of the sample substrate 20. Any scanning mechanism that produces a two-dimensional scan may be used to move the substrate along orthogonal axis in plane with the surface of the sample substrate.

The lens system 12 provides coaxial illumination of the sample substrate with the stimulating beam 11. The stimulating beam 11 is an excitation beam that stimulates fluorescent light emission from the sample substrate 20 at the illuminated spot: If there are areal fluorescent samples 23, 23' on the illuminated surface of the sample substrate stimulation of detectable fluorescent light results. The lens system 12 provides as well coaxial collection of the resulting fluorescent light and a fluorescent beam 29 is formed. To maximize collection efficiency, it is preferred that the lens system 12 has a large numerical aperture. The fluorescent light is then collected by the lens system 12, acting as a condenser, and directed as a retro-beam back along the incident light path (but in the opposite direction). Since the fluorescent light generally consists of a broad band of wavelengths different from the wavelength(s) of the incident stimulating beam, and since the system should be designed to work with a variety of fluorochromes, the system is preferably largely achromatic and provides correction of chromatic aberrations over a range of wavelengths. Light passing through the lens system 12 impinges upon a photodetector 31, such as a photomultiplier tube (PMT).

Whichever imaging system is used, it should preferably be capable of scanning at high speed over a large scan field with high resolution imaging and minimal optical aberrations. It should provide coaxial illumination and collection with high collection efficiency. An achromatic system with excellent color correction, as well as a system designed for minimizing background noise (including autofluorescence) is preferred.

Figure 2:
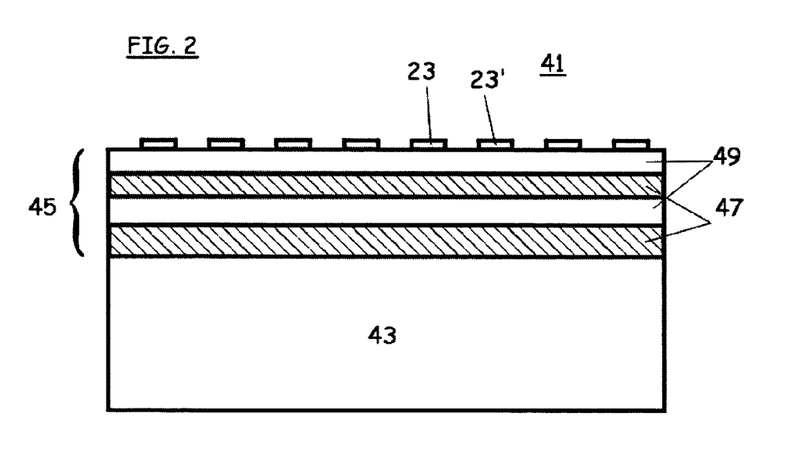
FIG. 2 is a close up side section view of a sample substrate of the present invention.

With reference to FIG. 2, a sample substrate 41 of the present invention comprises a base 43 and an interference reflector 45 on top of said base 43. The areal fluorescent samples 23, 23' are applied on top of said interference reflector 45.

The base 43 could be made of any material that can be coated. For example the base material can be transparent such glass or plastic or it can be metallic such as aluminum. The use of any other rigid bottom layer is possible.

The interference reflector 45 comprises a dielectric multilayer coating with at least one high index coating layer 47 and at least one low index coating layer 49.

As coating materials for example $Nb_2O_5$, $SiO_2$, aluminum oxide, magnesium oxide, oxides of the groups VIb, Vb; IVb, as well as scandium, yttrium, calcium, strontium, zinc, iron, indium, tin, cerium, holmium, as well as oxide of mixtures or alloys of these elements and further oxynitrides of the elements Ti, Ta, Zr, Si, Hf, Al, as well as fluorides of the elements Magnesium, Barium, Strontium, Calcium, the rare earths and lead can be used.

The layers may be coated for example by one of the following methods: thermal and/or electron beam vapor deposition, replication, transfer, film deposition, by processes of the CVD type (LPCVD, PECVD etc.) or of the PVD type such as sputtering, i.e. DC magnetron sputtering. Ion assisted deposition processes can be used as well as the sol-gel process. The layers may transferred onto the base by one of the following methods: bonding and molecular adhesion.

The top layer of the interference reflector 45 is not necessarily an inert material, but could be biologically active so as to bind with the sample material or a particular constituent of the sample.

In order to maximize the fluorescent emission by maximizing the electrical field at the location of the areal fluorescent sample, the layer thickness distribution of the multilayer coating comprised in the interference reflector 45 is to be optimized.

The optimization of the multilayer coating design can be done by applying one of the well known optical thin film calculation and optimization techniques. In most cases these techniques are based on minimizing a merit function which measures the distance of the spectral characteristics of the actual thin film design to the target characteristics. Within a slight modification of the standard process the merit function can be modified in such a way that it comprises a term which is addressing the distance of the square of the electrical field to a desired value, which equals in the present case the maximum value of the standing wave.

In order to correctly determine the proper coating thickness distribution and/or index distribution, the incident angle of the excitation light, the polarization and the refractive indices of the cover medium, of the coating material and of substrate must be taken into account.

Please note that with such an optimization method it is as well possible to design thin film stacks which meet the requirements of maximum field at the location of the areal fluorescent samples 23, 23' for excitations at two or more excitation wavelengths with the same multilayer coating. With the present invention it is therefore not necessary to compromise thicknesses to match the desired wavelengths.

The sample substrate 41 is designed to work with any fluorescence imaging system, for example like that shown in FIG. 1. The sample substrate 41 according to the present invention is constructed to maximize fluorescent emission and collection without having to increase the power of the laser beam and without having to change the objective or other optics in the system other than the substrate 41 itself.

As an example a multilayer coating is given comprising 22 layers. The coating layer material, layer thickness distribution as well as the index of refraction is listed in Table 1. For this example each individual layer thickness is designed using $Nb_2O_5$ (n=2.3) as material with a high optical refractive index and $SiO_2$ (n=1.48) as a material with a low optical refractive index. Other coating materials can be used. Multilayer coatings comprising more than two materials can be used as well. In the present example the design is optimized for an excitation wavelength of 532 nm.

Figure 3:
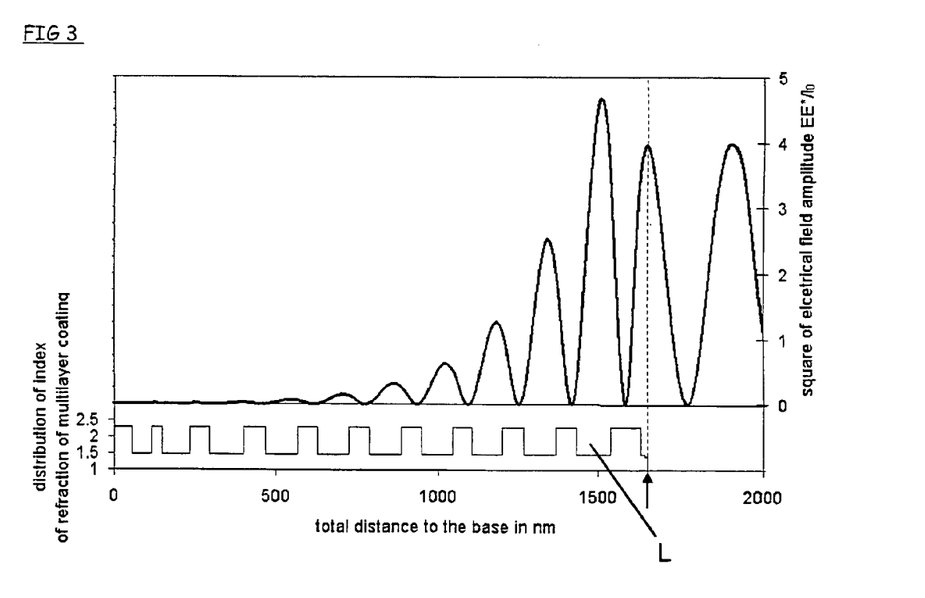
FIG. 3 is a graph showing the normalized square of the electrical field distribution $(E^2)/I_0^2$ versus distance from the base of the sample substrate shown in FIG. 2. In addition shown is the distribution of the index of refraction of the multilayer coating.

FIG. 3 shows schematically the resulting normalized square of the electrical field amplitude as a function of distance from the base 43. Shown as well is the distribution of the index of refraction as a function of the distance from the base 43. As can be seen in FIG. 3 the square of the electrical field within the interference reflector 45 is oscillating from zero to a local maximum value and back to zero. The envelope of the local maxima within the interference reflector is increasing with distance to the base. It is therefore not possible to identify a reflecting surface. Since the excitation light penetrates several wavelengths into the interference reflection, definition of a penetration depth is not useful for defining a reflection surface.

As seen in FIG. 3, in case the proper coating thickness is provided, the areal fluorescent samples 23, 23' is located at or near an antinode of the standing wave which is established above the interference reflector 45 when the stimulating beam is reflected. The location of the areal fluorescent samples is especially indicated with an arrow as well as with the broken line. With maximum excitation, maximum fluorescence occurs. Even if the coating thickness is not exactly correct for the excitation wavelength, if the intensity is only 90% or 95% of the peak intensity, the fluorescence signal will still be significantly improved over prior art sample substrates. Variations from the ideal thickness can occur due to sample-to-sample variation and coating variations.

Further, if two or more different excitation wavelengths are to be used with the same substrate sample, an optimization strategy of the multilayer coating can be chosen to reach maximum field at the location of the areal fluorescent samples for all excitation wavelengths required. Thus, avoiding the usage of any undesired locations of lower electrical field for any required excitation wavelength.

The fluorescence imaging system of FIG. 1 could have one or more light sources providing multiple fluorescence excitation wavelengths, either simultaneously or selectably, for different fluorescent sample constituents. The nominal optical thickness distribution of the multilayer coating needs and can then be optimized for each of the different excitation wavelengths in parallel for the same multilayer coating.

This is illustrated in more detail in the following example:

Here for the two excitation wavelengths Cy5 at 633 nm and Cy3 at 532 nm the sample substrate should provide enhanced electromagnetic field on the physical surface. In order to achieve this we proceed according to the following steps:

Designing of a first layer system, reflecting a first wavelength range (620 nm–650 nm) and transmitting a second wavelength range (520 nm–550 nm), thereby taking care that the outermost layer is an $SiO_2$ layer.

Adjusting the outermost layer in such a way, that the square amplitude electromagnetic field for the first excitation wavelength (633 nm) on the physical surface of the layer system is almost four times as high as the square of the amplitude electromagnetic field of the incoming propagating plane wave. With this the electromagnetic field conditions for the first excitation wavelength are optimum on the surface. The layer thicknesses for this first layer system are now fixed.

Placing an intermediate layer system between substrate and adjusting the layer thicknesses in order to reflect the second wavelength range.

Adjusting the thickness of the layer of the intermediate layer system which is adjacent to the first layer system in such a way, that the square amplitude electromagnetic field for the second excitation wavelength (532 nm) on the physical surface of the layer system is almost four times as high as the square of the amplitude electromagnetic field of the incoming propagating plane wave.

With this the electromagnetic field conditions for the second excitation wavelength as well as for the first excitation wavelength are optimum on the surface.

Table two shows one example of such a sample substrate optimized for enhancement for the two excitation wavelengths 532 nm and 633 nm.

Because of this possibility it can be even in the case of the existance of a well defined reflective surface (for example a metallic surface) as described by Kain et al of advantage to skip the quarterwave condition and to use a dielectric multilayer coating stack and the optimization process as described above to realize maximum fields at the location of the areal fluorescent samples for one more than one excitation wavelength.

This is illustrated in more detail in the following example:

The first excitation wavelength (633 nm) is reflected by the dielectric interference layers whereas the second excitation wavelength is reflected by the silver layer. The outermost layer of this coating layer system can be used to adjust the electromagnetic field of the first excitation wavelength on the physical surface by adjusting the layer thickness. The first layer on the silver coating can be used to adjust the electromagnetic field of the second excitation wavelength by adjusting the layer thickness. Table 3 gives an example of a thickness distribution of such a layer system.

In our examples we used always $SiO_2$ as outermost layer. This is the standard material for applying linker chemistry. Linker chemistries are quite sensitive to the materials used on the physical surface of the substrate sample. Therefore different linker chemistries might require outermost layers different from $SiO_2$. It is clear that the concept of the invention should not be limited to the use of $SiO_2$ as outermost layers. In practical examples we already used $TiO_2$ and/or $Nb_2O_5$. Any other practical optical coating material could be used as well. Additionally, in case the fluorescent emission is be detected from the backside of the substrate, the approach of the present invention can be used due to the absence of any metal layer incorporated. In this case the multilayer coating can be in addition optimized to effectively transmit the fluorescent light.

TABLE 1

| Layer number | Physical Thickness [nm] | Material | refractive Index |
|---|---|---|---|
| Substrate | — | BK7 | 1.52 |
| 1 | 55 | Nb2O5 | 2.3 |
| 2 | 64 | SiO2 | 1.48 |
| 3 | 33 | Nb2O5 | 2.3 |
| 4 | 82 | SiO2 | 1.48 |
| 5 | 63 | Nb2O5 | 2.3 |
| 6 | 104 | SiO2 | 1.48 |
| 7 | 67 | Nb2O5 | 2.3 |
| 8 | 98 | SiO2 | 1.48 |
| 9 | 61 | Nb2O5 | 2.3 |
| 10 | 96 | SiO2 | 1.48 |
| 11 | 64 | Nb2O5 | 2.3 |
| 12 | 100 | SiO2 | 1.48 |
| 13 | 63 | Nb2O5 | 2.3 |
| 14 | 97 | SiO2 | 1.48 |
| 15 | 61 | Nb2O5 | 2.3 |
| 16 | 97 | SiO2 | 1.48 |
| 17 | 64 | Nb2O5 | 2.3 |
| 18 | 102 | SiO2 | 1.48 |
| 19 | 62 | Nb2O5 | 2.3 |
| 20 | 106 | SiO2 | 1.48 |
| 21 | 94 | Nb2O5 | 2.3 |
| 22 | 10 | SiO2 | 1.48 |
| 23 | 10 | Linker chemistry | 1.4 |

TABLE 2

| Layer number | Physical Thickness [nm] | Material | refractive Index |
|---|---|---|---|
| Substrate | — | BK7 | 1.52 |
| 1 | 58.5 | Nb2O5 | 2.3 |
| 2 | 92.79 | SiO2 | 1.46 |
| 3 | 59.18 | Nb2O5 | 2.3 |
| 4 | 93.5 | SiO2 | 1.46 |
| 5 | 59.45 | Nb2O5 | 2.3 |
| 6 | 93.69 | SiO2 | 1.46 |
| 7 | 59.43 | Nb2O5 | 2.3 |
| 8 | 93.42 | SiO2 | 1.46 |
| 9 | 59.08 | Nb2O5 | 2.3 |
| 10 | 92.5 | SiO2 | 1.46 |
| 11 | 58.18 | Nb2O5 | 2.3 |
| 12 | 90.39 | SiO2 | 1.46 |
| 13 | 56.23 | Nb2O5 | 2.3 |
| 14 | 295 | SiO2 | 1.46 |
| 15 | 73.7 | Nb2O5 | 2.3 |
| 16 | 114.27 | SiO2 | 1.46 |
| 17 | 77.35 | Nb2O5 | 2.3 |
| 18 | 90.9 | SiO2 | 1.46 |
| 19 | 72.2 | Nb2O5 | 2.3 |
| 20 | 107.15 | SiO2 | 1.46 |
| 21 | 65.75 | Nb2O5 | 2.3 |
| 22 | 115.64 | SiO2 | 1.46 |
| 23 | 71.75 | Nb2O5 | 2.3 |
| 24 | 118.89 | SiO2 | 1.46 |
| 25 | 84.99 | Nb2O5 | 2.3 |
| 26 | 80 | SiO2 | 1.46 |
| 27 | 10 | Linker chemistry | 1.4 |

TABLE 3

| Layer number | Physical Thickness [nm] | Material | refractive Index |
|---|---|---|---|
| Substrate | — | BK7 | 1.52 |
| 1 | 100 | AG | |
| 2 | 90 | SiO2 | 1.46 |
| 3 | 73.7 | Nb2O5 | 2.3 |
| 4 | 114.27 | SiO2 | 1.46 |
| 5 | 77.35 | Nb2O5 | 2.3 |
| 6 | 90.9 | SiO2 | 1.46 |
| 7 | 72.2 | Nb2O5 | 2.3 |
| 8 | 107.15 | SiO2 | 1.46 |
| 9 | 65.75 | Nb2O5 | 2.3 |
| 10 | 115.64 | SiO2 | 1.46 |
| 11 | 71.75 | Nb2O5 | 2.3 |
| 12 | 118.89 | SiO2 | 1.46 |
| 13 | 84.99 | Nb2O5 | 2.3 |
| 14 | 80 | SiO2 | 1.46 |
| 15 | 10 | Linker chemistry | 1.4 |

What is claimed is:

1. A sample substrate adapted for use with fluorescence excitation light with a first wavelength, comprising a base and a reflector, the reflector comprising a reflecting multilayer interference coating with at least two layers wherein not all of the layers L fulfill a quarterwave condition: $d_L \cdot n_L = (2N+1) \cdot \lambda/4$ wherein $d_L$ is a physical thickness of layer L, $n_L$ is an index of refraction of layer L at the first wavelength, N is an integer equal to or greater than zero and $\lambda$ is the first wavelength, and wherein thicknesses of the layers ensure that any fluorescent sample material disposed on top of said multilayer interference coating is located near an antinode of a standing wave formed by the excitation light with the first wavelength incident on said substrate.

2. The sample substrate according to claim 1 further adapted for use with fluorescence excitation light with at least a second wavelength different from the first wavelength wherein the thicknesses of the layers ensure that the fluorescent sample material disposed on top of said multilayer interference coating would be located near an antinode of a standing wave formed by the excitation light with the second wavelength incident on said substrate.

3. The sample substrate according to claim 2, wherein said first wavelength is within the wavelength range of 532 nm to 548 nm and said second wavelength is around 633 nm.

4. The sample substrate according to claim 1 wherein the reflector is metal-free.

5. The sample substrate according to claim 1 wherein the base provides a metallic reflecting surface.

6. The sample substrate according to claim 1 wherein an outermost layer of the reflecting multilayer interference coating is a SiO$_2$ layer.

7. The substrate of claim 1 wherein the multilayer interference coating comprises a first layer system comprising multiple layers and an intermediate layer system comprising multiple layers, the intermediate layer system being disposed between the base and the first layer system.

8. The substrate of claim 7 wherein the first layer system transmits light at one of the wavelengths.

9. The substrate of claim 7 wherein the intermediate layer system comprises a metal layer disposed on the base and a dielectric layer disposed on the metal layer.

10. The substrate of claim 9 wherein the metal layer is one metal of the group comprising silver, gold, aluminum, chromium, platinum and any alloys of these metals.

11. The substrate of claim 1 wherein the multilayer interference coating comprises dielectric layers having alternately relatively higher and lower refractive indices such that an outermost layer is one of the layers having a relatively lower refractive index.

12. The substrate of claim 11 wherein the layers comprise at least one of Nb2O5, SiO2, aluminum oxide, magnesium oxide; oxides of the groups VIb, Vb, IVb, scandium, yttrium, calcium, strontium, zinc, iron, indium, tin, cerium, or holmium; oxides of mixtures or alloys of scandium, yttrium, calcium, strontium, zinc, iron, indium, tin, cerium, or holmium; and oxynitrides of Ti, Ta, Zr, Si, Hf, or Al; fluorides of magnesium, barium, strontium, calcium, rare earths, and lead.

13. The substrate of claim 11 wherein the layers comprise Nb2O5 and SiO2.

14. The substrate of claim 1 further comprising a linking coating disposed on an outermost layer of the reflector.

15. The substrate of claim 14 wherein the linking coating layer is biologically active.

16. The substrate of claim 1 wherein the base is rigid.

17. The substrate of claim 1 wherein the base comprises one of glass, plastic, metal, or semiconductor material.

18. Use of the substrate sample according to claim 1 in bioanalysis systems.

19. A fluorescence imaging system comprising a sample substrate according to claim 1 and a light source directed to the sample material on said sample substrate, said light including the fluorescence excitation wavelength and being particular to a specified fluorescent constituent of said sample material.

20. A laser scanner comprising a fluorescence imaging system according to claim 19.

21. A sample substrate, comprising:
a base, and
a reflector including a reflecting multilayer interference coating having a plurality of layers of which at least one layer does not fulfill a quarterwave condition, said quarterwave condition being defined as a physical thickness of said layer multiplied by an index of refraction of said layer equaling an odd multiple of one-quarter of a first wavelength;
wherein the sample substrate is adapted for use with fluorescence excitation light having said first wavelength and with fluorescence excitation light having a second wavelength that is shorter than said first wavelength,
wherein the reflector includes a first layer system for reflecting excitation light having said first wavelength and transmitting excitation light having said second wavelength, and a second layer system located between the first layer system and the base for reflecting excitation light having said second wavelength, and
wherein thickness of each layer of said plurality of layers ensure that a fluorescent sample material disposed on top of said multilayer interference coating is located near an antinode of a standing wave formed by excitation light incident on the substrate and having the first wavelength or the second wavelength.

* * * * *

UNITED STATES PATENT AND TRADEMARK OFFICE
CERTIFICATE OF CORRECTION

| | |
|---|---|
| PATENT NO. | : 7,227,633 B2 |
| APPLICATION NO. | : 10/858792 |
| DATED | : June 5, 2007 |
| INVENTOR(S) | : Jörg Kraus et al. |

It is certified that error appears in the above-identified patent and that said Letters Patent is hereby corrected as shown below:

Column 5, line 57 thru Column 6, line 2:  Please delete the entire last paragraph in Column 5, starting with the word "Provided" and which carries over to Column 6 and ends with the word "substrate."

Column 5, line 28 thru Column 5, line 40:  Please move the 4th full paragraph in Column 5, starting at line 28 with the word "Provided" and ending at line 40 with the word "substrate." so that it starts a new paragraph after the word "lengths." and becomes the second (2nd) paragraph under the subheading BRIEF SUMMARY OF THE INVENTION.

Column 11, TABLE 1:  Please insert the reference character --L--

Signed and Sealed this

Ninth Day of September, 2008

JON W. DUDAS
*Director of the United States Patent and Trademark Office*